United States Patent [19]
Eppler et al.

[11] Patent Number: 5,331,094
[45] Date of Patent: * Jul. 19, 1994

[54] PURIFIED ACTIVE SOMATOSTATIN RECEPTOR

[75] Inventors: Cecil M. Eppler, Langhorne, Pa.; John R. Zysk, Frenchtown; Martin J. Corbett, Mt. Holly, both of N.J.; Hong-Ming Shieh, Langhorne, Pa.

[73] Assignee: American Cyanamid Company, Wayne, N.J.

[*] Notice: The portion of the term of this patent subsequent to Jul. 6, 2010 has been disclaimed.

[21] Appl. No.: 963,246

[22] Filed: Oct. 19, 1992

Related U.S. Application Data

[63] Continuation of Ser. No. 677,009, Mar. 28, 1991, abandoned.

[51] Int. Cl.$^5$ .................. C07K 15/06; C07K 15/14
[52] U.S. Cl. ........................... 530/395; 530/350
[58] Field of Search ........................ 530/350, 395

[56] References Cited

U.S. PATENT DOCUMENTS 4,857,637  8/1989  Hammonds et al. ............. 530/403

OTHER PUBLICATIONS

Open reading frame expression vectors: A general method for antigen production in Escherichia coli using protein fusions to β-glactosidase. Proc. Natl. Acad. Sci. USA vol. 80, pp. 4432–4436, Jul. 1983 Genetics, G. M. Weinstock, et al.

Sawutz, David G. et al., "Glycosylation of the Mammalian α1-Adrenergic Receptor by Complex Type N–Linked Oligosaccharides," 1987, Mol. Pharmacol. 32:565–571.

Karl-Norbert Klotz and Martin J. Lohse, "The Glycoprotein Nature of A1 Adenosine Receptors". 1986. Biochem. and Biophys. Res. Commun. 140:406–413.

Jarvie, Keith R. et al., "Dopamine D2 Receptors Retain Agonist High–Affinity Form and Guanine Nucleotide Sensitivity after Removal of Sialic Acid". 1988. J. Biochem. 104:791–794.

Rauh, James J., et al., "Glycoprotein Properties of Muscarinic Acetylcholine Receptors from Bovine Cerebral Cortex". 1986. J. Neurochem. 46:23–32.

van Koppen, Chris J. and Nathanson, Neil M., "Site-Directed Mutagenesis of the m2 Muscarinic Acetylcholine Receptor". 1990. J. Biol. Chem. 265:20887-20892.

Breitfeld, Philip P., et al., "Influence of the N–Linked Oligosaccharides on the Biosynthesis, Intracellular Routing, and Function of the Human Asialoglycoprotein Receptor", 1984, J. Biol. Chem. 259:10414–10421.

Daniel, Thomas O., et al., "Biosynthetic and Glycosylation Studies of Cell Surface Platelet–derived Growth Factor Receptors". 1987. J. Biol. Chem. 262:9778–9784.

Cummings, Richard D., et al., "Biosynthesis of N– and O-Linked Oligosaccharides of the Low Density Lipoprotein Receptor". 1983, J. Biol. Chem. 258:15261–15273.

Cunningham, Roger K., Molecular Immunology. Marcel Dekker, Inc., 1984. p. 53.

Pilch, Paul F. and Czech, Michael P., "Affinity Cross-Linking of Peptide Hormones and Their Receptors". Membranes, Detergents and Receptor Solubilization. Alan R. Liss, Inc., 1984, pp. 161–175.

Feldman, Richard I., et al., "Purification and Characterization of the Bombesin/Gastrin-releasing Peptide Receptor from Swiss 3T3 Cells". 1990. J. Biol. Chem. 265:17364–17372.

Couvineau, Alain, et al., "Purification of Vasoactive Intestinal Receptor from Porcine Liver by a Newly Designed One-step Affinity Chromatography". 1990. J. Biol. Chem. 265:13386–13390.

(List continued on next page.)

Primary Examiner—Robert A. Wax
Assistant Examiner—Stephen Walsh
Attorney, Agent, or Firm—Estelle J. Tsevdos

[57] ABSTRACT

The invention relates to a purified somatostatin receptor which is purified at least about 30,000-fold over the receptor which is membrane-bound. The invention also provides pharmaceutical compositions containing the receptor and antibodies to the receptor.

5 Claims, 8 Drawing Sheets

OTHER PUBLICATIONS

Fishman, Jordan B., et al., "Purification and Characterization of the Rat Liver Vasopressin (V1) Receptor". 1987. J. Biol. Chem. 262:14049–14055.

Thermos, K., et al., "Biochemical Properties of Brain Somatostatin Receptors". 1989. Neuroscience 31:131–141.

Malbon, Craig C., et al., "Antibodies to Beta-Adrenergic Receptors". The β-Adrenergic Receptors. J. P. Perkins, ed. 1991. The Humana Press, Inc., pp. 181–185, 205.

Shapiro, Robert A., and Nathanson, Neil M., "Deletion Analysis of the Mouse m1 Muscarinic Acetylcholine Receptor: Effects on Phosphoinositide Metabolism and Down–Regulation". 1989. Biochemistry. 28:8946–8950.

Strader, Catherine D., et al., "Structural basis of β-adrenergic receptor function". 1989. The FASEB Journal. 3:1825–1832.

Schreiber, Alain B., et al., "Monoclonal antibodies against receptor for epidermal growth factor induce early and delayed effects of epidermal growth factor". 1981. Cell Biology. 78:7535–7539.

Roth, Richard A., et al., "Monoclonal antibodies to the human insulin receptor block insulin binding and inhibit insulin action". 1982. Cell Biology. 79:7212–7316.

Marion, S., et al., "Characterization of Monoclonal Antibodies to the Human Thyrotropin Receptor". 1992. Endocrinology. 130:967–975.

Yoshida, Tadashi, et al., "Monoclonal Antibodies to the Thyrotropin Receptor Bind to a 56–kDa Subunit of the Thyrotropin Receptor and Show Heterogenous Bioactivities". 1988. J. Biol. Chem. 263:16341–16347.

Shalaby, M. R., et al., "Binding and Regulation of Cellular Functions by Monoclonal Antibodies against Human Tumor Necrosis Factor Receptors". 1990. J. Exp. Med. 172:1517–1520.

Graziano, Michael P., et al., "Purified Rat Hepatic β2–Adrenergic Receptor". 1985. J. Biol. Chem. 260:7665–7674.

Bahouth, Suleiman W., et al., "Immunological approaches for probing receptor structure and function". 1991. TiPS. 12:338–343.

L. Dunbar Lewis et al., *Endocrinology* 121:486–492, 1987.

N. Kimura et al., *J. Biol. Chem.* 264:7033–7040, Apr. 25, 1989.

F. Reyl-Desmars et al., *J. Biol. Chem.* 264:18789–18795, Nov. 5, 1989.

H. T. He et al., *Proc. Nat. Acad. Sci.* 86:1480–1484, Mar. 1989.

M. Zeggari et al., *Eur. J. Biochem* 164:667–673, 1987.

S. Knuhtsen et al., *Biochem. J.* 254:641–647, 1988.

Reyl-Desmars et al., Chem. Abstr 110:124, #186, 391w, *C.R. Acad. Sci. Ser. 3,* 308(9): 251–254, (1989).

DunBar-Lewis et al, *Endocrinology* 121:486–492 (1987).

Kimura et al, *JBC* 264:7033–7040 (1989).

Reyl-Desmars et al, *J. Biol. Chem.* 264:18789–18795 (1989).

He et al., *PNAS* 86:1480–1484 (1989).

Zeggari et al, *Eur. J. Bch.* 164:667–673 (1987).

Knuhtsen et al, *Biochem. J.* 254:641–647 (1988).

PURIFIED ACTIVE SOMATOSTATIN RECEPTOR

This is a continuation of co-pending application Ser. No. 07/677,009 filed on Mar. 28, 1991, now abandoned.

BACKGROUND OF THE INVENTION

All vertebrates produce one or more different types of growth factors or growth hormones which are responsible for, among other effects, stimulating protein synthesis, cell division and growth, tissue formation, repair and/or maintenance, and storage or release of particular necessary nutrients into or out of specific cells. Such factors or hormones are often proteins or polypeptides they share the common feature of being manufactured and released by one type of cell, but exerting their ultimate effects on a different type of target cell. Among some of the better known growth mediators are nerve growth factor, epidermal growth factor, fibroblast growth factor, insulin-like growth factors (somatomedin) and growth hormone (somatotropin).

Each of these factors acts initially by binding to a receptor protein, which may be located either on the surface or in the cytoplasm of the particular factor's target cell. The receptor has a binding site which has a high affinity and specificity for the growth factor or hormone when the binding between factor and receptor occurs, a sequence of reactions is initiated which in some manner alters the functioning of the target cell. For example, it may cause the target cell to increase production and secretion of a particular protein, or alternately, it may signal the target cell to temporarily cease or decrease production of a certain protein.

Another example of a specific type of intercellular signalling compound is the peptide somatostatin, also referred to as somatotropin release-inhibiting factor (SRIF). This peptide is produced in a number of tissues, including the brain, gut, pancreas and adrenal cortex, and has wide-ranging effects throughout the body. As its name implies, SRIF inhibits the release of somatotropin from the anterior pituitary. However, other physiological effects of SRIF include inhibition of glucagon and insulin release from the pancreas, regulation of gut motility, and neurotransmission/neuromodulation function in the brain. In the latter capacity, SRIF can stimulate the release of neurotransmitters such as serotonin, dopamine and epinephrine. SRIF exists in two principle forms in mammalian tissues: SRIF-14, which is a tetradecapeptide, and SRIF-28, in which residues 15-28 are identical to SRIF-14. SRIF-28 also has an additional 14 amino acids at its amino terminus. The shorter peptide results from postranslational proteolytic cleavage of SRIF-28.

The intracellular aspect of the signalling action of somatostatin is mediated via receptors on the surface of target cells. It has been suggested that SRIF receptor subtypes exist in different cells and for differential interactions with specific signalling mechanisms. For example, radiological competition assays have shown that SRIF-14, SRIF-28 and other synthetic analogs can show vast differences in receptor binding affinity in brain, pancreas and pituitary cells (Srikant et al., Endocrinology 108:341-343, 1981; Tran et al., Science 228:492-495, 1985; Heiman et al., Neuroendocrinology 45:429-436, 1987; Amhardt et al., J. Clin. Invest. 80:1455-1460, 1987; Srikant et al., Nature 294:259-260, 1981). SRIF receptor subtypes are also suggested by the observation of differential effects of SRIF-14 and SRIF-28 on glucagon and insulin release in pancreas (Brown et al., Endocrinology 108:2391-2393, 1981) and on K+ channel activation in cultured cerebral cortical neurons (Wang et al., PNAS USA 86:9616-9620, 1989).

The activity of the SRIF receptor in mediating the SRIF biological effects seems to be intimately associated with pertussis toxin-sensitive GTP-binding regulatory proteins (hereinafter referred to as G proteins). It has been suggested (Jacobs et al., PNAS USA 80:3899-3902, 1983; Lewis et al. PNAS USA 83:9035-9039, 1985; Wang et al., PNAS USA 86:9616-9620, 1989) that SRIF receptors couple to cellular effector systems such as the adenylyl cyclase complex and to ion conductance channels by way of the G proteins. This association has been particularly well demonstrated in pituitary cells, wherein pertussis toxin blocked SRIF-mediated inhibitions of $Ca^{2+}$ influx (Lewis et al., supra, Reisine et al., J. Pharmacol. Exp. Ther. 235:551-557, 1985) and adenylate cyclase (Reisine et al., J. Pharmacol Exp. Ther. 232:275-282, 1985), reduced agonist binding affinity of the SRIF receptor (Reisine, Supra), and blocked the SRIF-mediated inhibiting of adenylate cyclase and $Ca^{2+}$ and decreased binding of $[^{125}I]Tyr^1$-SRIF by more than 95% (Kirk et al., Endocrinol. 114:1784-1790, 1984).

There has been evidence that direct immunoneutralization of SRIF enhances growth in primitive breeds of sheep (Spencer, Domestic Animal Endocrinology 3:55-68, 1985). However, this technique has had very limited success in commercial breeds of farm animals (Meats, Can. J. Anim. Sci. 70:1091-1097, 1990). This failure could be the result of compensatory overproduction of SRIF, variability in the immune response between animals or undesirable effects on other SRIF-dependent systems (i.e., lack of tissue specificity). However, the potentiation of growth hormone releasing factor effects in the rat model system by passive immunoneutralization of SRIF (Wehrenberg et al., Endocrinology 114:1613-1616, 1984; Wehrenberg et al., Biochem. Biophys. Res. Comm. 109:562-567, 1982) suggests that neutralization of SRIF, either pharmacologically or immunologically, has great potential. One way in which the problems with the antisomatostatin approach might be overcome is the specific antagonism of the SRIF receptor via receptor-specific ligands or antireceptor antibodies. Use of either one of these techniques involves binding a non-SRIF material to the receptor, thereby blocking the receptor site and preventing the sending of endogenous SRIF. However, to date there has been little success in synthesizing peptide SRIF antagonists, and a random screening procedure would be useful in identifying compounds that inhibit SRIF activity. Moreover, although the immunological approach is becoming a means of animal growth regulation, the appropriate tools for application of these methods to SRIF have not yet been developed. In each of these approaches, the availability of a purified, well-characterized, tissue-specific receptor is essential to successful use of the methods.

Notwithstanding the need in art for isolation of SRIF receptors generally, and a pituitary receptor in particular, there has been little progress made in conclusively solubilizing and purifying well-defined SRIF receptors from any tissue type. Purification of pituitary receptors in general has been difficult because of the scarcity of tissue, as well as the problems involved in solubilizing the receptors in active form and developing an efficient purification method. SRIF receptors from various cell sources have been solubilized (He et al., Mol. Pharmacol. 37:614–621, 1990; Knuhtsen et al., J. Biol. Chem. 265:1129–1133, 1990; Reyl-Desmars et al., J. Biol. Chem. 264:18789–18795, 1989) in active, high affinity states in the detergent CHAPS. SRIF Receptor: [$^{125}$I] SRIF complexes have also been solubilized in CHAPS (Knuhtsen et al., Biochem. J. 254:641–647, 1988) and Zwittergent (Zeggari et al., Eur. J. Biochem. 164:667–673, 1987). At best, however, these complexes were stable enough to allow chromatographic separation of free from bound radio-ligand, and no further purification of receptor was reported.

One attempt to purify the solubilized SRIF receptor from rat brain has been reported (He et al., PNAS USA 86:1480–1484, 1989). The authors employed affinity chromatography on immobilized D-Trp-SRIF14. Eluates from the affinity column were not shown to have SRIF binding activity. Nonetheless, these investigators concluded that the SRIF receptor had been isolated. This conclusion was based on the ability to chemically cross-link a [$^{125}$I]-labelled SRIF analog to a 55–60,000 MW protein in the eluate, and comparison with a similar sized protein which was radiolabelled by chemical cross-linking in intact brain membranes (Thermos and Reisine, Mol. Pharmacol 33:370–377, 1988). The human gut SRIF receptor from HGT-1 cells was said to be purified by a monoclonal antibody with apparent specificity for the SRIF receptor (Reyl-Desmars, et al., J. Biol. Chem. 264:18789–18795, 1989). Eluates from the immunoaffinity column showed binding of [$^{125}$I]SRIF, and also contained a single narrow 90,000 MW band. However, the affinity column eluates showed greatly lowered SRIF binding affinity, making characterization of the purified receptor less reliable. Also, the sharply focused 90K band was unusual for a presumably glycosylated protein. Proteins of this type usually give a poorly focused "fuzzy" appearance. No further information has been published on any of these putative receptors; therefore, their identity as such remains uncertain.

The present invention now provides a substantially pure SRIF receptor protein, the identity of which is verified by a number of different criteria. The receptor protein, which is purified by a novel method, is isolated substantially free of other associated proteins, including G proteins, and as such is useful for sequencing, gene cloning, antibody production, and therapeutic purposes.

SUMMARY OF THE INVENTION

The present invention relates to a substantially pure somatostatin (SRIF) receptor protein, and biologically active fragments thereof. The receptor is purified from 30,000 to 100,000-fold relative to the membrane-bound receptor. By "biologically active fragments" is meant natural or synthetic portions of the full length receptor which are essential in conferring immunogenicity to the molecule or which are themselves capable of binding receptor-specific ligand. In a preferred embodiment, the receptor is derived from human, rat, sheep, pig or cow. Somatostatin receptors are isolatable from pituitary, brain, gut, pancreas, liver and lung. In a particularly preferred embodiment, the receptor is derivable from pituitary tissue. The pituitary receptor is a heavily glycosylated glycoprotein with a molecular weight of about 75–95,000, preferably in the range of 80–90,000 daltons, with a core protein having a molecular weight of about 35–40,000 daltons.

The invention also relates to pharmaceutical compositions comprising an effective amount of the pure receptor or fragment in combination with a pharmaceutically acceptable carrier. The receptor and receptor fragments are useful in screening methods to identify somatostatin analogs, as well as identifying compounds which may act as somatostatin antagonists at the receptor site. They also are useful in raising somatostatin-receptor specific antibodies such antibodies may, by blocking the receptor site, effectively prevent somatostatin binding and thereby enhance growth. Pharmaceutical compositions containing the receptor or receptor fragments can be used to treat any disorder resulting from or associated with an excess of circulating somatostatin, such as pancreatic somatostatinoma, where diabetes mellitus, reduced growth hormone levels, and gut maladsorption result from excess circulating SRIF levels (Wass, in, Endocrinology, 2nd ed., Vol. 1:152–166, 1989; L. G. DeGroot, ed., W. B. Saunders Co.). Such compositions can be employed for in vivo administration to bind circulating somatostatin, also thereby preventing its binding to the endogenous receptor, and enhancing growth. The invention thus also relates to these therapeutic methods for regulating or modulating the action of somatostatin in vivo, by use of such pharmaceutical compositions.

The SRIF receptor of the present invention is isolated by a novel purification method. This method is claimed in U.S. Pat. No. 5,225,543, incorporated herein by reference in its entirety.

DETAILED DESCRIPTION OF THE INVENTION

As described in the subsequent Examples, SRIF receptor is isolatable in adequate quantity from rat $GH_4C_1$ cells, a pituitary cell line. However, the source of the receptor is not limited to these cells but in fact may be derived from any cell line or tissue expressing the receptor. Potentially useful pituitary cell lines would include the $GH_3$ rat pituitary tumor line (Yasumura et al., Science 154:1186, 1986) and the AtT-20 mouse pituitary tumor line (Sabol, Arch. Biochem. Biophys. 203:37-48, 1980). Other useful cell lines would be the HGT-1 human gastric carcinoma line (Laboisse et al., Cancer Research 42:1541-1548, 1982) and the rat pancreatic acinar cell line AR4-2J (Viguerie et al., Am. J. Physiol. 255:G113-G120, 1988). Useful tissues include intact pituitary, liver, and brain as well as isolated pancreatic acini from a number of species. The receptor is preferably derived from human, porcine, bovine, ovine and murine tissues or cell lines.

The receptor is isolated initially as a complex with its associated G protein. Although a variety of SRIF analogs are available and could be used as ligands for receptor binding, it is preferable that biotinylated SRIF analogs are prepared to be used as ligands for purification. A particularly preferred ligand is the analog referred to as BioS28 or BioSRIF28, which is biotinyl-NH-Leu8-DTrp22-Tyr25-SRIF28 (Peninsula Labs). In the preferred isolation method, the ligand is first bound to intact pituitary cell membranes to form a receptor=ligand (R:L) complex. After binding, the membranes are solubilized in detergent and intact receptor:ligand complexes are obtained. A particularly useful detergent for this purpose is a combination of deoxycholate and lysolecithin, preferably in a ratio of 1:1, at a concentration of 0.2% W/V or less. This assumes a membrane protein concentration of 1 mg/ml. At this stage, the receptor portion of the complex consists of the receptor and its associated G protein consisting of alpha, beta, and gamma subunits; this is confirmed by the rapid dissociation of the R:L complex in the presence of chelating agents EDTA and EGTA and a stable GTP analog (GTP-gamma-S). The recovery of soluble intact R:L complex is generally in the range of 40-70% of that initially present in the membranes after the binding step.

Figure 3:
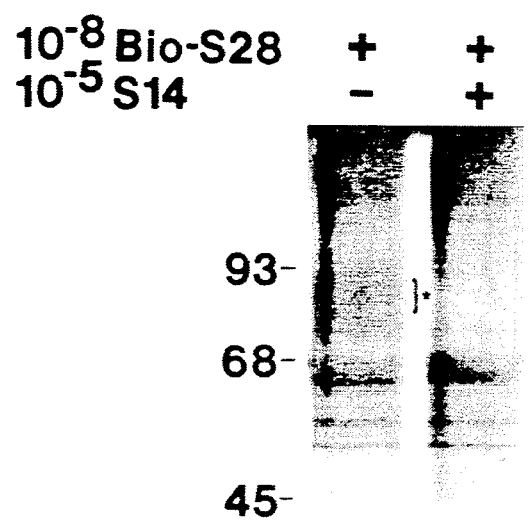
FIG. 3 illustrates the EDTA/EGTA/GTP-gamma-S eluate from a streptavidin column run on 12% SDS-PAGE. The diffuse band with molecular weight of between 75–95,000 daltons represents the SRIF receptor glycoprotein, while the two narrowly focused bands, molecular weights of 40,000 and 35,000, are the associated G protein subunits.

The solubilized R:L complex is then contacted with streptavidin-agarose (SA-A), whereby the biotinylated portion of the R:L complex will tightly bind to the streptavidin. Streptavidin is preferred, due to its lower non-specific binding; however, free and immobilized avidin is also available (Pierce, Vector) and may be suitable for some purposes. The SA-A is eluted with EDTA, EGTA and GTP-gamma-S. GTP-gamma-S serves to dissociate the G protein from its the receptor, thereby lowering the affinity of the receptor and indirectly causing dissociation from the ligand. EDTA and EGTA may add to this effect and also directly interfere with ligand binding, which depends on divalent cations. The eluate (in which the receptor is purified to a level of at least about 25-30%), when run on 12% SDS-PAGE, shows a diffuse band, the glycoprotein receptor, with a molecular weight of about 75,000-95,000 daltons, and two narrow bands, having molecular weight of about 40,000 and 35,000 daltons, representing two of the dissociated G protein subunits, $G_i$- or $G_o$-alpha and G-beta, respectively (FIG. 3). The presence of the G protein subunits provides further evidence of the identity of the larger protein as the SRIF receptor. The SRIF receptor band and the two G protein subunits do not appear in eluates from control SA-A columns done with SRIF receptors loaded with non-biotinylated S14. Electroelution at this stage yields intact glycoprotein at a purity of about 80-90%. Although this level of purification may be adequate for analytical purposes such as amino acid sequencing, in an alternate embodiment, it is desirable to further purify the receptor by lectin affinity chromatography rather than gel electrophoresis. This is a high efficiency, high purification step which yields a receptor of 90% or greater purity (as judged by SDS-PAGE). The protein core of the receptor can be obtained from this preparation by removal of carbohydrate by the enzyme endoF and purification of the core receptor by SDS-PAGE or reverse phase HPLC. This final purification of the protein core yields a 35-40,000 MW core receptor.

Additional experiments, utilizing non-biotinylated radiolabelled SRIF analog ligands, are conducted to independently confirm true receptor isolation and to further characterize the chemical nature of the receptor. A [$^{125}$I]Tyr11-S14 analog is used as described above, to create soluble R:L complexes from $GH_4Cl$ membranes. These complexes are applied to wheat germ agglutinin (WGA) and eluted with N-N'-N"-triacetylchitotriose. About 82% of the original soluble R:L complex is recovered in the eluate, confirming that the isolated material is expected to be a glycoprotein (Table 3).

In a second experiment, a (Leu-8,Trp-22[$^{125}$I]-Tyr25)S28 analog ([$^{125}$I S28]) is chemically cross-linked to the receptor, solubilized, and the complex then adsorbed to WGA-agarose and eluted as noted above. On SDS-PAGE, the eluate shows the radiolabelled receptor as a broad band having a molecular weight of about 80-100,000 daltons (FIG. 6), with about 3,000 daltons being due to the presence of the ligand.

To obtain a more accurate molecular weight of the protein core of SRIF receptor, the cross-linking of [$^{125}$I S28] with the receptor is followed by deglycosylation with the enzyme endoF (a 1:1 mixture of endoglycosidase F and N-glycosidase F in either one of two ways.

First, deglycosylation is carried out on SDS-solubilized membranes before electrophoresis. The final product has a molecular weight of about 38,000 daltons (FIG. 7), in contrast to the diffuse band described above. Alternately, the radiolabelled R:L complex is first separated by gel electrophoresis, removed from the gel by electroelution, and then deglycosylated before final separation by gel electrophoresis. The result is essentially the same as with the crude membrane proteins, although the final product forms a broader band of 35–40,000 daltons, possibly due to incomplete deglycosylation or from chemical heterogeneity caused by processing.

Thus, based on data from the putative purified receptor and the radiolabelled cross-linked SRIF analogs, the pituitary SRIF receptor is confirmed as a glycoprotein with a molecular weight of about 75–95,000. MW of the glycosylated receptor inherently falls in a broad range due to microheterogeneity of the attached oligosaccharide groups. Approximately 50% of the apparent molecular weight of the protein is due to carbohydrate, with the core receptor protein having a molecular weight of about 35,000–40,000 daltons.

The purified receptor, or biologically active fragments thereof, can be used for a number of purposes. For example, the purified material, in either glycosylated or unglycosylated form, can be used to create monoclonal or polyclonal antibodies having specificity for the SRIF receptor. The technology for creation of monoclonal antibodies is well known in the art (see, e.g., Goding, Monoclonal Antibodies: Principles and Practice, 2nd Ed., 1986). Such antibodies may have utility in tumor localization and therapy: it has recently been reported that SRIF analogs have proven useful in imaging certain receptor-bearing endocrine tumors (Lamberts et al., N. Engl. J. Med., Nov. 1, 1990, 1246-1249). It is reasonable to anticipate that detectably-labelled antireceptor antibodies can serve the same purpose, by targeting SRIF receptor sites. They can also be used in tumor therapy, preferably in conjugated form with antitumor or cytotoxic drugs or radioisotopes, which by their association with the antibody, will be targeted directly to cancerous cells expressing large amounts of receptor.

Anti-receptor antibodies can also be administered in a passive immunization protocol, to bind receptor, thus blocking SRIF from binding to receptor sites. This ultimately should enhance growth of the host so treated. To a similar end, the receptor can be used in the preparation of anti-idiotypic antibodies. Such antibodies would bind to circulating SRIF, thus preventing its binding to receptor sites.

Pharmaceutical compositions containing the receptor and/or active fragments thereof, in combination with a pharmaceutically acceptable carrier, may also be prepared. In one embodiment, such compositions will contain an amount of receptor and/or fragment effective to bind circulating SRIF, thereby preventing it from interacting with endogenous receptors in vivo. In a second embodiment, the composition contains an immunogenic amount of receptor or fragment; such compositions, when administered in vivo to an animal, may be used to raise anti-receptor autoantibodies that will bind to endogenous receptors, thereby preventing circulating SRIF from binding the receptors. Such immunological methods are disclosed in U.S. Pat. No. 4,857,637, relating specifically to the use of growth hormone (somatotropin) receptors; the contents of this patent are incorporated herein by reference. The effect in both of these cases is to inhibit the effects of SRIF, thereby leading to increased release of somatotropin, and ultimately increased growth of the animal so treated. Other effects of SRIF may similarly be altered, such as its effect on release of neurotransmitters and gut motility. Administration of the compounds is preferably parenteral, i.e., intramuscular, intravenous and intraperitoneal or subcutaneous; choice of carrier can be made in accordance with the preferred mode of administration, and formulation and dosage are within the ability of the skilled artisan.

The isolated receptor protein itself can be used in screening assays to identify compounds that act as analogs. For example, the receptor protein can be immobilized by any means which does not interfere with SRIF binding activity. The immobilized receptor is then contacted with a specific compound or mixture and its ability to compete with radiolabelled SRIF for binding to the receptor is evaluated. Variations on this method will be apparent to those skilled in the art.

The present invention encompasses the SRIF receptor protein and its biologically active fragments produced by any means, whether synthetically, recombinantly, or by purification of the native protein. The isolated SRIF receptor, as described above, is pure enough to be used in protein sequencing procedures which are well known in the art, and such sequencing is routinely accomplished using such methods. The protein sequence in turn is used to design oligonucleotide probes which are used to screen λgt10 libraries containing the relevant cDNA (copies of RNA), e.g., from $GH_4C_1$ pituitary cells. Hybridization of oligos with the library identifies the clone(s) containing the SRIF receptor gene or portions thereof. The gene or gene fragments are isolated from the clones, the whole gene reconstructed and then ligated into an appropriate vector by known methods. The vector is chosen based upon the choice of preferred host cell. The host cell may be prokaryotic, i.e., bacterial, such as *E. coli*, or eukaryotic, i.e., yeast, insect, or mammalian cells.

The following non-limiting examples further illustrate the present invention.

EXAMPLES

I. Methods

Unless otherwise stated, the following are used in the examples provided below:

A. Synthesis of Peptides—Four biotinylated SRIF analogs are synthesized. Two analogs, biotinyl-[NH—(CH$_2$)$_5$—CO]—NH-(Tyr11)SRIF14 (="Bio-6C—S14") and biotinyl-[NH—(CH$_2$)$_5$—CO]$_2$—NH-(Tyr11)SRIF14 (="Bio-12C-S14") are synthesized at Applied Biosystems, Foster City, Calif. Bio-6C-S14 is synthesized on solid phase by the FMOC method. Bio-12C-S14 are synthesized on solid phase by the TBOC method. The aminocaproate spacers are added by use of BOC-aminocaproate with DCC-HOBT coupling. The N-terminal biotin is also coupled by DCC-HOBT. Biotinyl-NH-(Leu8, D-Trp22, Tyr25)SRIF28 is synthesized at Peninsula Labs, Belmont, Calif., on solid phase by the t-BOC method. Biotin is coupled to the N-terminal by DCC-HOBT. Biotinyl-NH-SRIF14 is synthesized at American Cyanamid, Agricultural Research Division, Princeton, N.J. This is done on solid phase by the t-BOC method. Biotin is coupled to the N-terminus by DCC-HOBT.

B. Pituitary Cell Culture—GH$_4$C1 rat pituitary tumor cells are initially grown as monolayers in 82.5% Dulbecco's MEM (Gibco)+15% heat inactivated horse serum +2.5% heat inactivated fetal bovine serum (sera from CC Labs, Cleveland, Ohio)+50 units/ml penicillin +50 ug/ml streptomycin. The cells are then placed in suspension culture by replacement of MEM by suspension culture medium (MEM modified for suspension culture of "S-MEM", Gibco) and culturing in spinner flasks (Bellco, Vineland, N.J.). The concentration of horse serum is gradually reduced to 11% and the medium is supplemented with HEPES buffer and extra glucose. The medium finally developed for optimal growth of the GH$_4$C1 cells in suspension culture is as follows (expressed in % of total volume per liquid component): 84.5% DMEM +11% horse serum+2.5% fetal bovine serum+1% HEPES buffer (pH 7.4; 10 mM final conc.) +1% penicillin/streptomycin solution (5,000 units/ml pen+50 ug/ml strep) +0.7% 45% glucose solution. Cells are grown at 37° C. in the presence of 6% $CO_2$. Cultures are initially seeded at $1.5$-$2 \times 10^5$ cells/ml and grown to concentrations of $6$-$10^5$ cells/ml (3-4 days growth). Cells are passed by dilution or complete medium change every 3-4 days. Viability is greater than 95% by trypan blue staining.

C. Membrane Isolation—1-8 liter batches of cells at densities of $6$-$10 \times 10^5$ cells/ml are pelleted in conical bottom glass centrifuge bottles (600 or 800 ml; Bellco) at $1,000 \times g$ for 5 min. The supernatants are carefully poured off and the cells are resuspended in ice cold homogenization medium (1 mM Na-bicarbonate at pH 7.6, 1 mM EDTA and 1 mM EGTA) containing 0.7% (vol/vol) of the "$100 \times 4$pase" protease inhibitor cocktail (see below). Twenty ml of homogenization medium is used for every liter of suspension culture. After 5 min. on ice, the hypotonically swollen cells are homogenized with 10 strokes of a tight fitting Dounce homogenizer (Kontes, type A pestle). The homogenate is centrifuged at $1,000 \times g$ for 10 min. and the supernatant is removed and kept on ice. The $1,000 \times g$ pellet containing residual intact cells, nuclei and DNA is washed by gently homogenizing with 4 strokes with a type B pestle in one half the original volume of homogenization medium and recentrifuging for 10 min. at $1,000 \times g$. The final $1,000 \times g$ pellet consists mostly of DNA and is discarded. The $1,000 \times g$ supernatants are combined and centrifuged at $20,000 \times g$ for 30 min. The $20,000 \times g$ pellet is washed twice in 25 mM Tris (pH 7.4), with centrifugation for 25 min. at 20,000 2 g. Final membrane pellets are resuspended in 25 mM Tris buffer to concentrations of 4-10 mg membrane protein/ml. Then the $100 \times 4$pase protease inhibitor cocktails are added to 1% of final volume and aliquots are frozen on dry ice. Membranes are stored at $-90°$ C. until needed. Membrane protein is assayed with the Bradford dye binding assay (Bio-Rad).

D. Protease Inhibitor Mixtures—Three different protease inhibitor mixtures were used for receptor binding assays and receptor purification. A. $40 \times$ PMSF (phenylmethyl sulfonyl fluoride)/Baci=2 mg/ml PMSF (Bachem) +2 mg/ml bacitracin (Sigma) dissolved in DMSO. B. $400 \times$ PMSF/Bacitracin=20 mg/ml PMSF and 20 mg/ml bacitracin. Mixtures A and B are used in routine binding assays and in the binding step of the receptor purification protocol. The $40 \times$ concentration is generally used for smaller binding assays where pipetting accuracy of smaller volumes is a factor. Final DMSO concentrations in the binding assays, 0.25-2.5% do not affect ligand binding or any subsequent procedures. C. $100 \times 4$Pase —7.5 mg/ml leupeptin (Bachem) +14.5 mg/ml PMSF=3 mg/ml chymostatin (Bachem)+1 mg/ml pepstatin A (Sigma) dissolved in DMSO. This mixture is used in membrane solubilization buffers and in all buffers used in receptor purification. All protease inhibitor mixtures are stored as frozen aliquots at 4°-10° C. and are added to buffers at appropriate dilutions immediately before use.

E. Receptor Binding Methods

1. Standard Binding Assays—Binding assays are done in a binding buffer containing 50 mM HEPES (pH 7.4), 0.5% BSA and 5 mM $MgCl_2$. The standard assay for [$^{125}$I]SRIF analog binding to GH$_4$C$_1$ membranes, done in 96 well microtiter plates (Dynataech Immulon II Removawell plates), is carried out as follows: 1. Radioligand is diluted in binding buffer+ PMSF/Baci to the desired cpm per vol. of 50 $\mu$l and then 50 $\mu$l aliquots are added to the wells. For non-specific binding samples, 5 $\mu$l of 40 $\mu$M cold S14 is also added per well. 2. Binding is initiated by adding 150 $\mu$l per well of membrane diluted to the desired concentration (10-30 ug membrane protein/well) in binding buffer+ PMSF/Baci. Plates are then covered with Linbro mylar plate sealers (Flow Labs) and placed on a Dynatech Microshaker II and binding is allowed to proceed at room temperature for 1-2 hours. Binding is stopped by centrifuging the plate for 15 minutes at $2,000 \times g$. The supernatants are dumped off and membrane pellets washed once by addition of 200 $\mu$l of ice cold binding buffer, brief shaking and recentrifugation. Finally the individual wells are placed in $12 \times 75$ mm tubes and counted in an LKB Gammamaster counter (78% efficiency). Specific binding by this method is identical to that measured when free ligand is removed by rapid (3-5 seconds) filtration and washing on polyethyleneimine-coated glass fiber filters.

Three variations of the standard binding assay are also used:

2. competitive radioligand binding assays with a concentration range of cold ligand vs. [$^{125}$I]SRIF are carried out as described above with one modification. All dilutions of SRIF analogs being assayed are made in $40 \times$ PMSF/Baci to a concentration $40 \times$ the final concentration in the assay. This gives very consistent results with a wide variety of SRIF structural analogs over a wide range of dilutions. 5 ul samples of peptide are then added per microtiter well. Membranes and radioligand are diluted out in binding buffer without protease inhibitors. Radioligand is added and mixed with cold peptides and then binding is initiated by addition of membranes.

3. Chemical cross-linking of radioligand with receptor is done after a binding step identical to the standard assay. However, the wash step is done with binding buffer minus BSA to reduce the possibility of non-specific cross-linking of radioligand with BSA. The cross-linking step is carried out as described below.

4. Larger scale binding assays to obtain membrane pellets for studies on solubilization of receptor: ligand complex and for receptor purification are also carried out. These are identical to the standard assays except that: (a) Binding is carried out in polypropylene tubes in volumes from 1-250 ml, (b) Concentration of membrane protein is always 0.5 mg/ml, (c) For receptor purification, BSA concentration in the binding buffer is reduced to 0.25% and the wash step is done with binding buffer without BSA. This is to reduce BSA contamination of the purified receptor.

F. Chemical Cross-Linking of Radioligand to Receptor—After a radioligand binding step as described above ("Receptor Binding Methods, 3."), the membrane pellets are resuspended in 200 ul per microtiter plate well of ice-cold binding buffer without BSA. Then 5 ul per well of 4 mM N-5-azido-2-nitrobenzoyloxysuccinimide (ANB-NOS, Pierce) in DMSO is added and mixed. The samples are held on ice and UV-irradiated for 10 minutes with a Mineralight R-52G lamp (UVP Inc., San Gabriel, Calif.) at a distance of 5–10 cm. Then the samples are transferred to Eppendorf microfuge tubes, the membranes pelleted by centrifugation, supernatants removed and membranes solubilized in Laemmli SDS sample buffer for polyacrylamide gel electrophoresis (PAGE). PAGE is done as described below and radiolabelled proteins are visualized by autoradiography of the dried gels with Kodak XAR film and Dupont image intensifier screens.

G. Membrane Solubilization—Initial solubilization studies are carried out in buffer containing 25 mM Tris (pH 8), 10% glycerol (wt. vol.) and 0.2 mM $CaCl_2$. Later, $MgCl_2$ is substituted for $CaCl_2$, as mentioned in the text. This will be referred to as "solubilization buffer". The highly soluble detergents including Triton X-100, deoxycholate, deoxycholate:lysolecithin, CHAPS and zwittergent are made up in solubilization buffer at 10% concentrations and stored as frozen aliquots. Lysolecithin is made up fresh because of insolubility upon freeze-thawing and digitonin is made fresh at lower concentrations due to its more limited solubility.

To solubilize membranes, washed pellets after the binding step are resuspended free of visible particles by pipetting and vortexing in solubilization buffer+100,000×g for 30 minutes. The supernatants are removed and held on ice and the pellets are discarded.

H. Assay of Solubilized Receptors—After binding of [$^{125}$I]SRIF analogs and solubilization of the membranes with detergent, the intact R:L complex could be assayed by four different methods (all carried out on ice or in a cold room at 4°–10° C.): (1) Column chromatography (Knuhtsen et al., Biochem. J. 254:641–647, 1988). Sephadex G-50 columns (8×250 mm) are equilibrated with solubilization buffer containing detergent at the concentration used to solubilize membranes and 1 mg/ml bovine serum albumin. 0.2–0.5 ml samples of solubilized membranes are applied to the columns and eluted at a flow rate of about 0.7 ml/minute. 0.18 ml samples are collected. Radioactivity is determined in a gamma counter as described under "Receptor Binding Methods". Void volumes of the columns are determined by the elution volume of blue dextran. Radioactivity eluting in the void volume (>50,000 MW) was considered bound to protein. Radioactivity eluting later, at the same volume as free [$^{125}$I]SRIF, is considered non-bound. (2) Polyethyleneglycol precipitation (Cuatrecasas, PNAS USA 69:318–322, 1972) For a 100 ul sample of solubilized membranes in a 12×75 mm polypropylene tube, 0.5 ml of 1% (w/v) bovine gamma globulin (Sigma) in 0.1M sodium phosphate buffer is added, followed by 0.5 ml of 25% (w/v) polyethyleneglycol (Sigma) and mixing. The mixture is held on ice for 15 minutes. Then 3 ml of 0.1M sodium phosphate (pH 7.4) is added per sample and the samples are rapidly (1–3 seconds) filtered over Whatman GF/B glass fiber filters and washed with 4 ml of the phosphate buffer. PEG precipitated SRIF receptor:[$^{125}$I]SRIF complex is determined by gamma counting of the filters. (3) GFB/PEI filter binding (Bruns et al., Analytical Biochem. 132:74–81, 1983). Whatman GF/B glass fiber filters are soaked in 0.3% polyethyleneimine (PEI, Sigma) for 3 hours. 25–100 ul samples of solubilized membranes are replaced in 12×75 mm polypropylene tubes. Then 4 ml of solubilization buffer (without detergent) is added per sample and the samples are immediately filtered through the GFB/PEI filters (1–3 seconds) and washed with 4 ml of solubilization buffer. CPM of SRIF receptor:[$^{125}$I]SRIF complex adsorbed to filters are determined by gamma counting. (4) Charcoal/Dextran (Paul and Said, Peptides 7[Suppl. 1]:147–149, 1986). 0.5 gm of Dextran T70 (Pharmacia) is dissolved in 1 liter of water and then 5 gm of activated charcoal (Norit A, alkaline; Fisher Scientific) is added. The suspension is stirred for 10 minutes at room temperature and then stored at 4° C. until use. To measure R:L complex, 4 parts by volume of charcoal/dextran suspension are added to 1 part by volume of solubilized membrane. The samples are mixed and held on ice for 2 minutes and then centrifuged for 2 minutes at 11,000×g in a Beckman microfuge. Free radioligand is adsorbed charcoal/dextran and is discarded with the pellet. SRIF receptor:[$^{125}$I]SRIF complex remain in the supernatant and is determined by gamma counting.

I. Receptor Purification

1. Binding of biotinyl-SRIF to $GH_4C1$ membranes. The binding step is carried out as described in Section 4 of "Receptor Binding Methods". Incubations are for 1 hour at room temperature. In the standard purification protocol, the binding incubations contain 10 nM Bio-S29/ [$^{125}$I]Bio-S28 is added as a tracer at levels of 5,000–100,000 cpm per mg of membrane protein. Control incubations contain 10 uM cold S14 to saturate the receptor with non-biotinylated ligand.

2. Solubilization of receptor:ligand complex. This is done as described ("Membrane Solubilization"), with 0.15% deoxycholate:lysolecithin in solubilization buffer containing 0.2 mM $MgCl_2$, to obtain 100,000×g supernatants containing solubilized R:L complex.

3. Adsorption of solubilized R:L complex to streptavidin. Immobilized streptavidin (streptavidin cross-linked to 6% beaded agarose, Pierce Chemical Co.; "SA-agarose") is washed in solubilization buffer and added to the solubilized membranes as 1/30 of the final volume. This mixture is incubated with constant stirring by end-over-end rotation for 4–5 hours at 4°–10° C. Then the mixture is applied to a column and the non-bound material is washed through. Binding of radioligand to SA-agarose is determined by comparing cpm in the 100,000×g supernatant with that in the column effluent after adsorption to SA-agarose. Finally, the column is washed with 12–15 column volumes of solubilization buffer+0.15% deoxycholate:lysolecithin +1/500 (vol/vol) 100×4pase.

4. Elution of streptavidin column. The column is eluted with solubilization buffer+0.1 mM EDTA+0.1 mM EGTA+0.1 mM GTP-gamma-S (Sigma)+0.15% (wt/vol) deoxycholate:lysolecithin +1/1000 (vol/vol) 100×4pase. First, one column volume of elution buffer is passed through the column and flow is stopped for 20–30 minutes. Then 3–4 more column volumes of elution buffer are passed through. All the eluates are pooled.

5. Wheat germ agglutinin purification of receptor—Eluates from the streptavidin column are incubated overnight (12-15 hours) with immobilized wheat germ agglutinin (WGA agarose, Vector Labs) to adsorb the SRIF receptor via interaction of covalently bound carbohydrate with the WGA lectin. The ratio (vol/vol) of WGA-agarose to streptavidin column eluate is generally 1:400. A range from 1:1000 to 1:200 gave very similar results. After the binding step, the resin is pelleted by centrifugation, the supernatant is removed and saved, and the resin is washed 3 times (about 2 minutes each) in buffer containing 50 mM HEPES (pH 8), 5 mM $MgCl_2$ and 0.15% deoxycholate:lysolecithin. To elute the WGA-bound receptor, the resin is extracted three times by repeated mixing (vortex mixer on low speed) over a 15-30 minute period on ice, with 3 resin columns each time, of 10 mM N-N'-N''-triacetylchitotriose in the same HEPES buffer (vide supra) used to wash the resin. After each elution step, the resin is centrifuged down and the supernatant is carefully removed, free of WGA-agarose pellets. The three, pooled eluates contain the final, purified SRIF receptor. The material non-bound to WGA contain G protein subunits specifically eluted from the streptavidin column plus non-specific contaminants. All these fractions are stored frozen at $-90°$ C.

J. Miscellaneous Preparative and Analytical Methods

1. SDS-polyacrylamide gel electrophoresis. Electrophoretic separation of proteins, solubilized in 1% SDS (in Laemmli sample buffer)+5 mM dithiothreitol for 5-10 minutes at 90° C., is done in 12% SDS-polyacrylamide gels by the method of Laemmli (Nature 227:680-685, 1970). Stacking gels are composed of 3.8% polyacrylamide. For regular silver staining of proteins bands the gels are fixed in 40% methanol+10% acetic acid and then stained with the Bio-Rad silver staining kit (Bio-Rad Labs). For silver staining of glycoproteins, the gels are stained by the method of Jay et al. (Analytical Biochem. 185:324-330, 1990), with prestaining by the dye alcian blue. This method is necessary for silver staining of heavily glycosylated proteins such as the SRIF receptor.

2. Concentration and extraction of protein samples for analysis. Prior to gel electrophoresis, amino acid analysis and sequencing, samples are concentrated in Centricon-30 microconcentrators (Amicon Co.). One to two ml samples are placed in the microconcentrator tubes and centrifuged at $3,000 \times g$ to pass excess buffer through the filters. Samples are concentrated to volumes of 50-150 ul and transferred to 1.5 ml, Eppendorf microfuge tubes. Then the samples are extracted in $CHCl_3:MeOH:H_2O$ to remove detergents and buffer and obtain a dry protein pellet (Wessel and Flugge, Analytical Biochem. 138:141-143, 1984). This pellet could be solubilized in SDS sample buffer for PAGE or in other solvents such as 70% formic acid or 8M urea for other purposes such as generation of proteolytic peptides, amino acid analysis and sequencing.

3. Preparation of radioligands for receptor binding assays. SRIF analogs are radioiodinated by the chloramine-T method. The reagents are added to 1.5 ml siliconized Eppendorf centrifuge tubes as follows: (a) 5 ul of peptide (0.5 mg/ml) in 50 mM potassium phosphate buffer (pH 7.4), (b) 5 ul of 100 mM potassium phosphate buffer (pH 7.4), (c) 5 ul of methanol, (d) 4 ul of $Na[^{125}I]$ (Amersham, 100 uDi/ml; cat.=IMS.30), mix by vortexing. add reagent (e) 5 ul of 0.7 mM chloramine-T (Kodak), mix by vortexing and allow 20 seconds reaction time, add (f) 5 ul of 2 mM tyrosine in 0.1% TFA. Immediately after reaction, the samples are injected onto a Supelco LC-308 column (c-8 reverse phase, 5 u particle size, 300 angstrom pore size, column dimensions=$0.46 \times 5$ cm). Labelled peptides are eluted isocratically at 20-26% acetonitrile (depending on the peptide) in water/0.1% TFA. Monoiodinated SRIF analogs are very efficiently separated by noniodinated peptide by this method. We have established this by kinetic studies with nonradioactive iodide and correlation with radiolabelling patterns. Therefore, the monoiodinated analogs are considered to have specific radioactivities of 2,200 Ci/mmole, the same as $[^{125}I]$. 0.1 ml radioactive peptide fractions off the column are collected into 0.1 ml volumes of 2% BSA in 1% acetic acid. The most active fractions are pooled, aliquoted and stored frozen at $-20°$ C.

II. RECEPTOR ISOLATION USING BIOTINYLATED LIGANDS

Receptor-Binding Characteristics of Biotinyl-SRIF Analogs

Four biotinylated SRIF analogs are synthesized ("Methods: Synthesis of Peptides"). Their structures and abbreviated designations are as follows:

Biotinyl-NH-SRIF14=Bio-S14
Biotinyl-[NH—$(CH_2)_5$—CO]—NH-(Tyr11)-SRIF14=Bio-6C-S14
Biotinyl-[NH-$(CH_2)_5$-CO]$_2$-NH-(Tyr11)-SRIF14=Bio-12C-S14
Biotinyl-NH-(Leu8, D-Trp22, Tyr25)SRIF28=Bio-S28

Figure 1A:
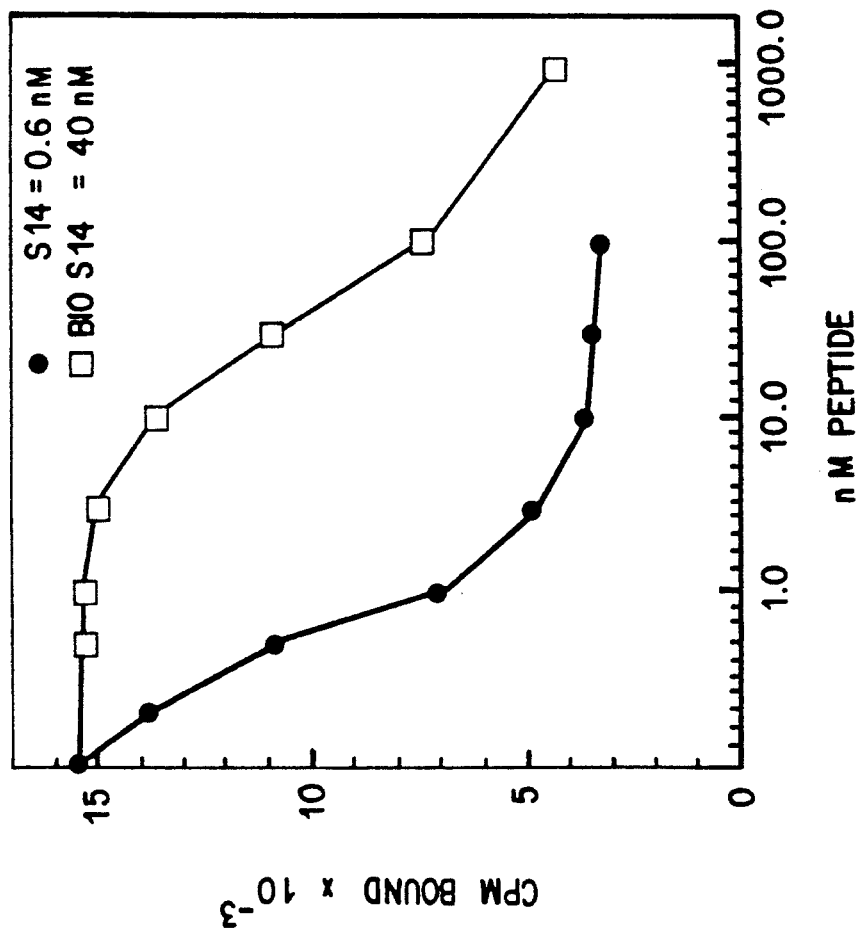
FIG. 1A and FIG. 1B illustrate the relative potencies of various synthetic biotinylated SRIF ligands in a competitive binding assay with non-biotinylated ligands. (A) shows a comparison with biotinylated ligand with no spacer; (B) shows a comparison of biotinylated ligands with spacers.
Figure 1B:
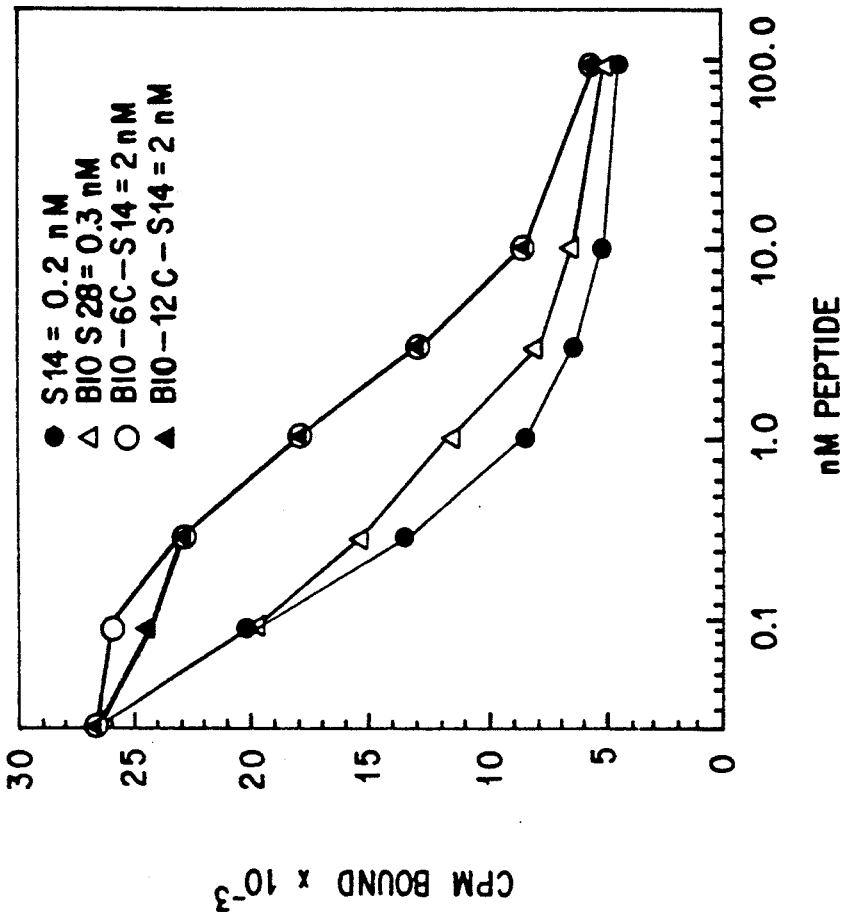

FIG. 1 shows the potencies of these peptides relative to each other and to S14 in competitive binding assays with $[^{125}I]$Tyr11-S14 and $GH_4C_1$ membranes. These assays are carried out as described in "Methods: Receptor Binding Methods, 2". The first SRIF analog synthesized, Biotinyl-NH-S14, contains no spacer between the biotinyl and S14 moieties and has only about 1.5% the potency of S14 in the competitive binding assay (FIG. 1A; assays contained to 40 ug of $GH_4C_1$ membrane protein and 85,000 cpm of radioligand). Therefore the Bio-6C-S14, Bio-12C-S14 and Bio-S28analogs are preferably synthesized. In Bio-S28, amino acid residues 1-14 are considered a spacer since residues 15-28 are equivalent to an S14 analog, having all the necessary structure for high affinity binding. The three spacer-containing biotinyl SRIFs show receptor binding activity similar to that of S14 (FIG. 1B; assays contained 20 ug of $GH_4C_1$ membrane protein and 100,000 cpm of radioligand). The $IC_{50}$s and relative potencies are S14 (0.2 nM)>Bio-S28(0.3 nM) >Bio-6C-S14 (2 nM)>Bio-12C-S14 (2 nM).

Figure 2:
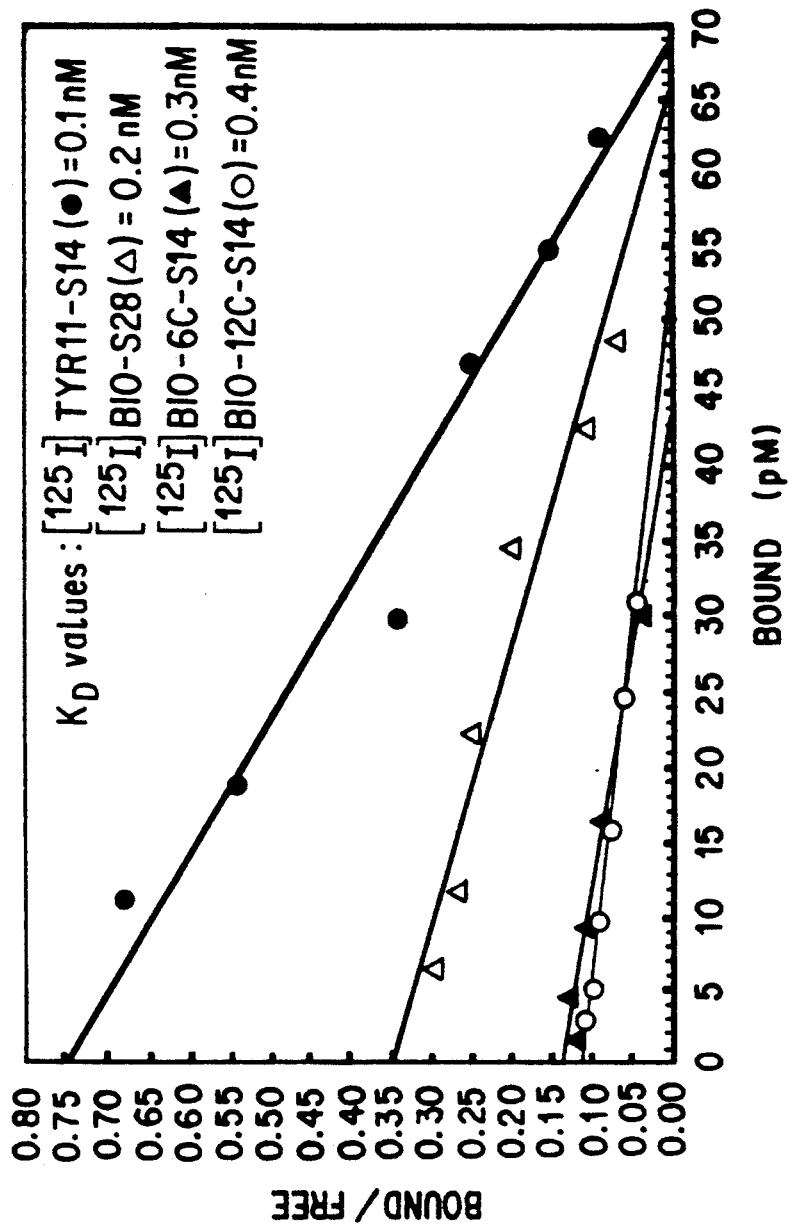
FIG. 2 illustrates a comparison of the relative binding affinities of three biotinylated ligands compared with a non-biotinylated ([$^{125}$I]Tyr11-S14) ligand.

Because Bio-C6-S14, Bio-C12-S14 and Bio-S28 all contain tyrosine residues, it is possible to prepare their $[^{125}I]$ labelled analogs and carry out Scatchard analyses of their binding affinities relative to $[^{125}I]$Tyr11-S14 (FIG. 2). As shown in the figure, the $[^{125}I]$-labelled peptides fall in the same order of potency as their non-labelled forms. The dissociation constants (KDs) and relative binding affinities are $[^{125}I]$Tyr11-S14 (0.1 nM)>$[^{125}I]$Bio-S28 (0.2 nM)>$[^{125}I]$Bio-6C-S14 (0.3 nM)>$[^{125}I]$Bio-12C-S14 (0.4 nM).

Streptavidin Binding Characteristics of Biotinyl-SRIF Analogs

The three, high-affinity binding, biotinyl-SRIF analogs (Bio-6C-S14, Bio-12C-S14 and Bio-S28) all appear to be useful for SRIF receptor purification. However, Bio-S28 is selected for further use in SRIF receptor purification because it binds to the SRIF receptor with the highest affinity (FIGS. 1 and 2) and because the solubilized R:L complex made with [$^{125}$I]Bio-S28 binds somewhat better to immobilized streptavidin than the R:L complexes with Bio-6C-S14 and Bio-12C-S14 (see Table 1).

To compare the three biotinyl-SRIF analogs in terms of binding to streptavidin, the following experiment is done. [$^{125}$I]Bio-SRIF analogs are bound to GH$_4$C$_1$ membranes as described ("Methods: Receptor Binding Methods, 3"). All radioligands are at a concentration of 0.77 to $10^6$ cpm/ml. For each radioligand, a control for non-specific binding was done in the presence of 1 uM cold S14. CPM bound/mg membrane protein after the binding step are as follows: [$^{125}$I]Bio-6C-S14=755,020 (total) and 43,361 (non-specific); [$^{125}$I]Bio-12C=S14=633,134 (total) and 39,538 (nonspecific); [$^{125}$I]Bio-S28=1,065,512 (total) and 35,049 (nonspecific). The membrane pellets are solubilized in solubilization buffer containing 0.15% deoxycholate:lysolecithin and 0.2 mM MgCl$_2$ as described ("Methods: Membrane Solubilization"). It should be noted that Mg$^2$ can replace Ca$^{2+}$ in the solubilization buffer, giving equally effective recovery of intact R:L complex and reducing the possibility of Ca$^{2+}$-dependent proteolysis. One ml samples of solubilized membranes are incubated with 0.05 ml vols of streptavidin-agarose at 4°–10° C. on a tube rotator for the times shown. Non-specific binding samples are not done due to the low levels of non-specific binding. At the times shown, the 8A beads are spun down and 100 ul samples of supernatant are counted. The cpm are compared to initial cpm in the sample and % binding to SA is calculated from this. The results are presented in Table 1. Also, it should be noted that binding of cpm from the supernatant is considered to parallel the binding of R:L complex. Several observations confirm that this is a valid assumption.

TABLE 1

Binding of [$^{125}$I]-Labelled Biotinyl-SRIFs to Immobilized Streptavidin
CPM are determined for 100 ul samples of initial 100,000 × g supernatant (containing soluble R:L complex) and supernatant after incubation with SA-agarose for the times shown.

| | | % Binding of Radioligand to SA-Agarose = (CPM Non-bound/Initial CPM) | | | |
|---|---|---|---|---|---|
| | | 1 hour | | 3 hours | |
| Radioligand | Initial CPM | CPM | % Bound* | CPM | % Bound |
| [$^{125}$I]Bio-6C-S14 | 63,490 | 28,381 | 55% | 16,228 | 74% |
| [$^{125}$I]Bio-12C-S14 | 54,344 | 23,391 | 57% | 13,071 | 76% |
| [$^{125}$I]Bio-S28 | 92,534 | 31,645 | 66% | 17,098 | 82% |

*Calculated as 100% - [(Non-bound CPM/Initial CPM) × 100%)

Purification of SRIF Receptor

A preparation of SRIF receptor is purified from 17 mg GH$_4$C$_1$ pituitary cell membranes as described in "Methods: Receptor Purification". Some important features of this experiment are as follows: Two 17 mg samples of membranes are used. Both are incubated with $10^{-8}$M Bio-S28. However, one sample also receives $10^{-5}$M non-biotinyl S14 for 2–3 minutes before addition of any Bio-S28. This serves to block binding of Bio-S28 and creates a control to show non-specific binding of proteins to the streptavidin column. Also, each sample receives $1.5 \times 10^8$ cpm of [$^{125}$I]Bio-S28 as a tracer. This is added 2–3 minutes before the addition of cold Bio-S28. After a 1-hour binding step, the membranes are washed in binding buffer without BSA and solubilized in solubilization buffer containing 0.15% deoxycholate:lysolecithin and 0.2 mM MgCl2. Each 100,000×g supernatant (17 ml) is incubated with 0.6 ml of streptavidin-agarose for 4 hours at 4°–10° C. The SA-agarose is transferred to a 0.7 cm diameter column, washed and eluted with EDTA/EGTA/GTP-gamma-S as described ("Methods: Receptor Purification").

Radioligand is followed through the procedure to estimate solubilization of R:L complex and % initial binding of R:L complex to immobilized streptavidin. This is shown in Table 2 below.

TABLE 2

Use of [$^{125}$I]Bio-S28 to Trace SRIF R:L Complex During Purification on Immobilized Streptavidin

| Ligand in Binding Step | CPM Initially Bound to Membranes | CPM Solubilized by Deoxycholate: Lysolecithin | Solubilized CPM Non-Bound to Streptavidin |
|---|---|---|---|
| $10^{-8}$ M Bio-S28 | 59,132 | 54,094 (91%) | 14,960 (28%) |
| $10^{-8}$ M Bio-S28 + $10^{-5}$ M S14 (NSB) | 9,316 | 6,834 (73%) | 1,054 (15%) |

A calculation from Table 2 shows that 72% of the specifically bound radioligand is bound to streptavidin. As discussed above, this should approximate the binding of R:L complex to streptavidin.

EDTA/EGTA/GTP-gamma-S is used to elute SRIF receptor from streptavidin columns because the soluble R:L complex is dissociated by this combination of agents. For the SRIF R:L complex solubilized in 0.15% deoxycholate:lysolecithin, 0.1 mM EDTA+0.1 mM EGTA+0.1 mM GTP-gamma-S gives 75–90% dissociation. This is probably due to initial dissociation of G-protein from the receptor and consequent lowering of ligand binding affinity.

The EDTA/EGTA/GTP-gamma-S eluates from streptavidin are concentrated by Centricon-30 filters and solvent extraction and then solubilized in SDS and separated on 12% SDS-polyacrylamide gels ("Methods: Miscellaneous preparative and Analytical Methods, 1, 2"). Staining of the gels by alcian blue/silver ("Methods: ibid") reveals three protein bands that are specifically bound to and eluted from streptavidin (FIG. 3). One is a diffuse, 75–95,000MW band. The two other specific bands are more sharply focused and had MWs of about 40,000 and 35,000. There are several non-specific bands that also appear in the sample where specific binding of Bio-S28 is blocked by a 1000-fold excess of non-biotinylated S14 ("$+10^{-5}$ S14" in FIG. 3).

Figure 4:
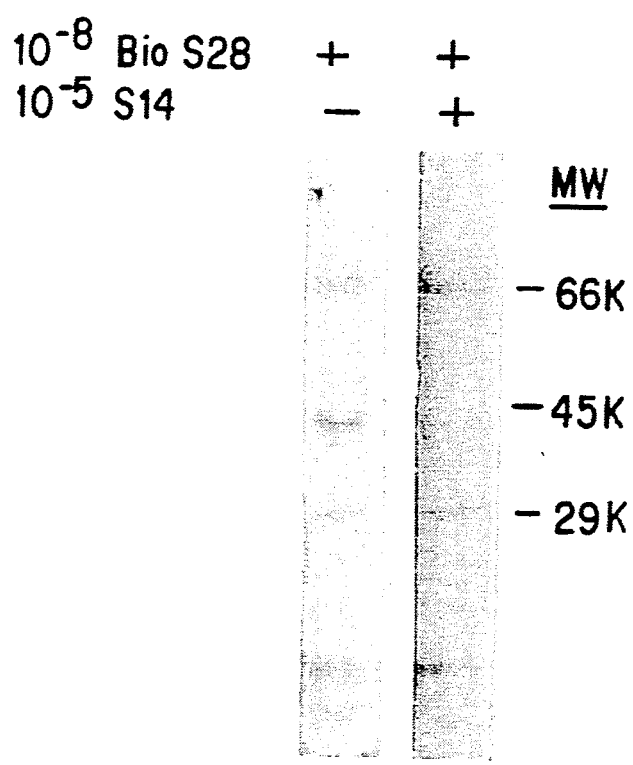
FIG. 4 illustrates the results of an experiment in which samples equivalent to those shown in FIG. 6 are reacted with pertussis toxin and [$^{32}$P]NADH (see text); [$^{32}$p] labelled proteins are separated on 12% SDS-PAGE and visualized by autoradiography. A protein of about 40K is only seen in the sample with Bio-S28 specifically bound ("$-10^{-5}$ S14") prior to purification of receptor on SA-A, confirming the identity is a G protein.

The 40K and 35K proteins have appropriate sizes for G protein alpha and beta subunits respectively. The 40K protein is functionally identified as a G-alpha subunit by the technique of ADP-ribosylation (FIG. 4). Here, pertussis toxin catalyzes transfer of [$^{23}$P]ADP-ribose from NADH to protein. This reaction is shown to be highly specific for G-alpha subunits of the "i" and "o" subtypes (Stadel and Lefkowitz, ibid). In FIG. 4, [$^{32}$p] labelling of a 40K protein in the presence of pertussis toxin and [$^{32}$P]NADH occurs in the streptavidin eluates with samples initially incubated with $10^{-8}$M Bio-S28 but not if Bio-S28 binding is blocked by excess non-biotinylated S14.

Figure 5:
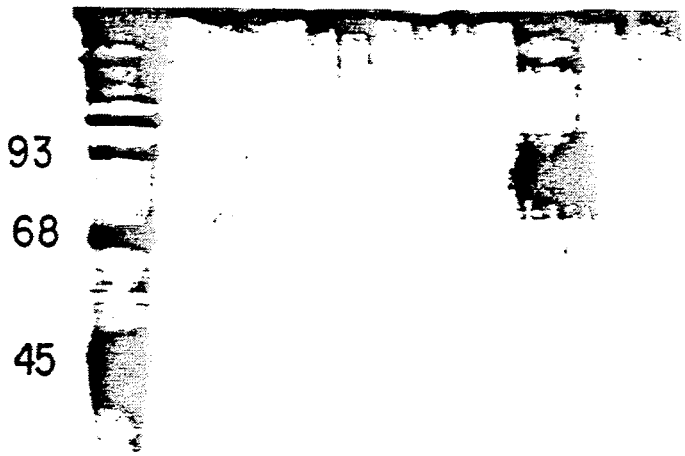
FIG. 5 illustrates the contents of the EDTA/EGTA/GTP-gamma-S eluate after application to WGA agarose and elution with 10 mM sugar. A diffuse band showing the expected molecular weight glycoprotein is clearly shown when the WGA eluate is run on 12% SDS-PAGE.

Finally, if the EDTA/EGTA/GTP-gamma-S eluate from streptavidin is incubated with immobilized wheat germ agglutinin (WGA-agarose), the putative, 75-95K SRIF receptor binds and can be eluted in nearly pure form by 10 mM N-N'-N''-triacetylchitotriose (FIG. 5; WGA binding and elution done as in "Methods: Receptor Purification. 5"; SDS-PAGE and alcian blue/silver staining done as previously described). FIG. 5 shows 1% of a purified sample obtained from 750 mg of $CH_4C_1$ membrane protein. We can consistently obtain SRIF receptor of this purity by the methods described herein.

III. OTHER MEANS OF RECEPTOR CHARACTERIZATION COMPARISONS WITH PURIFIED RECEPTOR

Confirmatory experiments are conducted to verify isolation of the same receptor by traditional binding methods and to further verify the chemical nature of the receptor. As the results show, a glycoprotein of identical molecular weight is identified by these methods as well. The ligands used in the following experiments are [$^{125}$I]Tyr11-S14 and (Leu8, D-Trp22, [$^{125}$I]Tyr25)S28, hereinafter referred to as "radiolabelled S28").

Lectin Affinity Binding

A. Solubilized Receptor: [$^{125}$I]Tyr11-S14 Complex-Binding of [$^{125}$I]Tyr11-Sir to $GH_4C1$ membranes is carried out as in "Receptor Binding Methods. 4". Binding incubations contain 0.5 mg/ml membrane protein and $6 \times 10^6$ cpm/ml of [$^{125}$I]Tyr11-S14. Solubilization of membranes in 0.15% deoxycholate:lysolecithin is also as previous described. Incubations for binding to WGA-agarose included 5 vol. of solubilized membrane ($100,000 \times g$ supernatant)+1 vol. of WGA-agarose. Binding proceeds for 2 hours at 4° C. with constant agitation. After binding to WGA, the supernatants are removed and replaced with equal volumes of solubilization buffers, 0.15% deoxycholate:lysolecithin, protease inhibitors, and 4 mM N-N'-N''-triacetylchitotriose. Elution is carried out for 1 hour and the supernatants are removed. Intact R:L complex in these and other solubilized samples are assayed by the GFB/PEI filter method ("Methods: Assay of Solubilized Receptors, 3"). The results are shown in Table 3, indicating the glycoprotein nature of the bound material. In this experiment, 82% of the initial solubilized R:L complex is recovered in the eluate from the WGA resin. The ratios of total bound to non-specifically found ligand (A/B) show that WGA specifically selects for the SRIF receptor. Thus, the ratio of total to non-specific binding increases about 4-fold from intact membranes to the eluate from WGA agarose. The same trend occurs with the R:L complex as measured by adsorption to GFB/PEI filters.

TABLE 3

| Sample | CPM of [$^{125}$I]Tyr11-S14 | | |
|---|---|---|---|
| | A. Total[1] | B. Non-Specific[2] | A/B |
| Membranes | 151,848 | 28,812 | 5.3 |
| 100,000 × g supernatant | 104,420 | 12,756 | 8.2 |
| Non-bound to WGA-agarose | 23,112 | 9,624 | 2.4 |
| Bound to WGA-agarose | 69,889 | 3,157 | 22.1 |
| Eluted from | 58,925 | 2,524 | 23.0 |

TABLE 3-continued

| WGA-agarose | | |
|---|---|---|
| Recovery of Soluble R:L Complex: CPM of Soluble [$^{125}$I]Tyr11-S14 Bound to GFB/PEI Filters | | |
| A. Total | B. Non-specific | A/B |
| — | — | — |
| 45,307 | 4,005 | 11.3 |
| 5,787 | 1,998 | 2.9 |
| — | — | — |
| 34,829 | 1,032 | 33.7 |

B. Chemically Cross—linked Receptor: Radiolabelled S28 Complex-The binding phase is carried out as noted above under "Receptor Binding Methods: 3". Chemical cross-linking is carried out as described in "Methods: Chemical Cross-linking of Radioligand to Receptor". Binding incubations are done in the presence or absence of $10^{-6}$M cold S14. The membranes are then solubilized in solubilization buffer as defined above, with 0.15% deoxycholate:lysolecithin and protease inhibitors. Binding of solubilized material to WGA-Agarose is achieved by incubating 5 volumes of solubilized membrane (100×g supernatant) with one volume of WGA- agarose. Binding proceeds for 2 hours at 4° C. with constant agitation. After binding to WGA, the supernatants are removed and replaced with equal volumes of solubilization buffer, 0.15% deoxycholate:lysolecithin, protease inhibitors, and 4 mM N-N'-N''-triacetylchitotriose. Elution is carried out for 1 hour and the supernatants removed.

Figure 6:
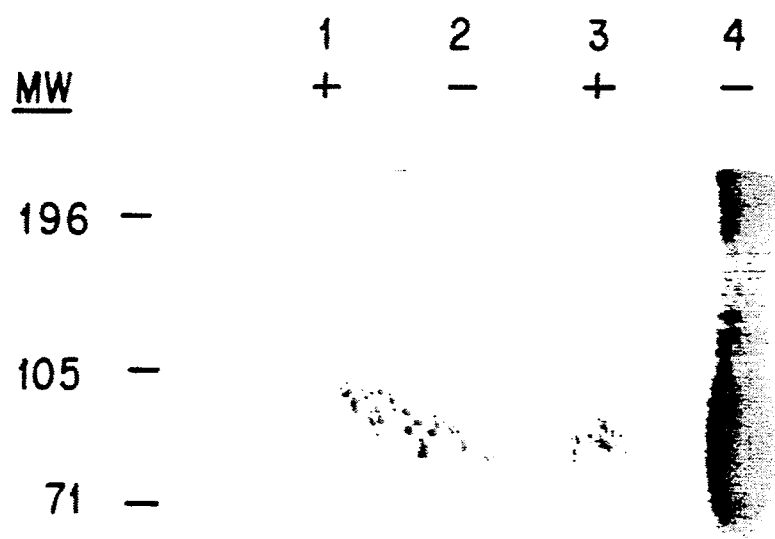
FIG. 6 illustrates the chemical cross-linking of (Leu8,DTrp22, [$^{125}$I]Tyr25)S28 to the SRIF receptor and interaction of the solubilized, cross-linked R:L complex with wheat germ agglutinin. Binding of the [$^{125}$I] labelled S28 analog to GH$_4$C$_1$ membranes and chemical cross-linking of the radiolabelled R:L complex with ANB-NOS are as described in "Methods". Binding incubations are done in the presence ("+") or absence ("−") of $10^{-6}$M cold S14. The membranes are then solubilized in solubilization buffer +0.15% deoxycholate:lysolecithin+protease inhibitors. Binding of solubilized material to WGA-agarose and elution with N-N'-N"-triacetylchitotriose ("TAC") are as described in the text. Prior to SDS-PAGE on 12% gels, the samples are concentrated on Centricon-30 filters and extracted in $CHCl_3$:MeOH:$H_2O$ as described in "Methods". Exposure time is 14 days. The numbered samples are shown in pairs + or $-10^{-6}$ cold S14 in binding incubations and are as follows: 1,2=Non-bound to WGA-agarose, 3,4=Eluted from WGA-agarose by 4 mM TAC.

Prior to SDS-PAGE on 12% gels, the samples are concentrated on Centricon-30 filters, extracted in $CHCl_3:MeOH:H_2O$. These methods were carried out as described in "Methods: Miscellaneous Preparative and Analytical Procedures 1 and 2". The radiolabelled proteins on the dried gels are visualized by autoradiography at −70° C. with DuPont intensifying screens. Exposure time is 14 days. FIG. 6 shows the radiolabelled SRIF receptor as a broad band with a molecular weight of 75-95,000 daltons, as observed using biotinylated ligands. The specificity of this band is shown by the complete lack of radiolabelling in membranes incubated with [Leu8, D-Trp22 [$^{125}$I]Tyr25)S28 and $10^{-6}$M cold S14 (+ lanes, 1 and 3). The glycoprotein nature of the receptor is clearly shown by the fact that it is deleted from the 100,000×g supernatants after exposure to WGA-agarose (lane 2) and was eluted from the WGA resin by N-N'-N''-triacetylchitotriose (lane 4).

Figure 7A:
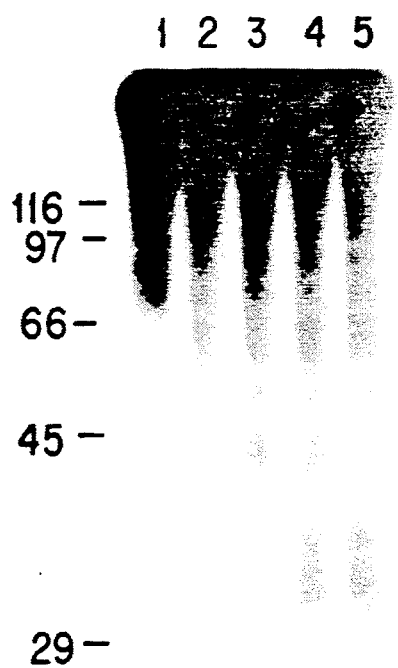
FIG. 7A and FIG. 7B illustrate deglycosylation of SRIF receptor:[$^{125}$I]S28 cross-linked complexes with endoF. A.=deglycosylation of radiolabelled cross-linked R:L complex in membranes. "Control", lane 1=no enzyme; lanes 2-5=0.2, 0.5, 1 and 2.5 ul of endoF. Visualization of labelled proteins by autoradiography. B. The R:L complex is first separated by SDS-PAGE, electroeluted, and the deglycosylated before final electrophoresis.
Figure 7B:
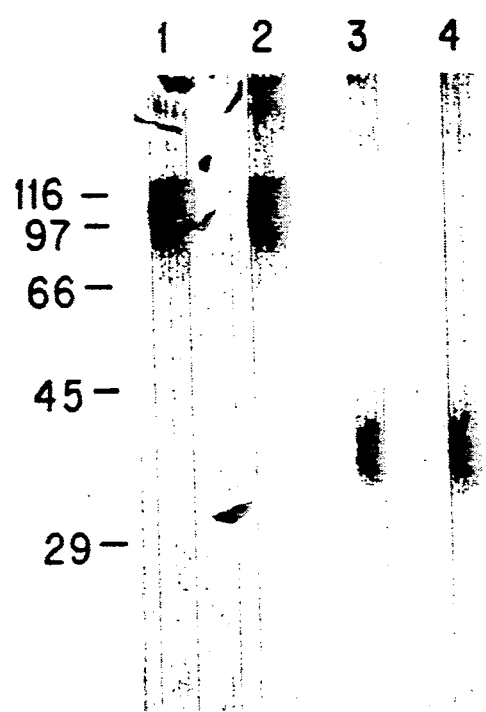

For a more accurate molecular weight determination of the SRIF receptor, the cross-linking of radioligand to the receptor is followed by deglycosylation with the enzyme endoF (a 1:1 mixture of endoglycosidase F and N-glycosidase F (Boehringer). This is carried out in two different ways. FIG. 7A shows the patterns obtained when deglycosylation is carried out on SDS-solubilized membranes prior to electrophoresis. The final product is a relatively tight band with a molecular weight of about 38,000. This contrasts sharply with the large, relatively diffuse band of intact receptor (FIG. 7A). In FIG. 7B, the radiolabelled receptor:ligand complex is first separated by gel electrophoresis, then removed from the gel by electroelution and then deglycosylated before final gel electrophoresis. This result is essentially the same as with the crude membrane proteins, but the final product formed a broader band with a molecular weight of about 35–40,000, possibly due to incomplete deglycosylation or chemical heterogeneity caused by processing.

What we claim is:

1. A substantially pure somatostatin receptor, sufficiently free of associated proteins so as to be suitable for protein sequencing, which receptor is purified at least 30,000-fold relative to a whole cell non-solubilized membrane bound receptor and in glycosylated form as a molecular weight of between 75,000–90,000 daltons and consists of a 35,000–40,000 dalton core when not glycosylated.

2. The receptor of claim 1 which is a pituitary receptor.

3. The receptor of claim 1 which is a glycoprotein having a molecular weight of about 75,000–95,000 daltons.

4. The receptor of claim 3 having a molecular weight of about 80,000–95,000 daltons.

5. The receptor of claim 1 which is at least about 90% pure.

* * * * *